United States Patent
Chen et al.

(10) Patent No.: US 11,175,211 B2
(45) Date of Patent: *Nov. 16, 2021

(54) SYSTEMS AND METHODS FOR ANALYZING NATURAL GAS FLOW IN SUBTERRANEAN RESERVOIRS

(71) Applicant: Saudi Arabian Oil Company, Dhahran (SA)

(72) Inventors: Huangye Chen, Cypress, TX (US); Hui-Hai Liu, Katy, TX (US)

(73) Assignee: Saudi Arabian Oil Company, Dhahran (SA)

( * ) Notice: Subject to any disclaimer, the term of this patent is extended or adjusted under 35 U.S.C. 154(b) by 156 days.

This patent is subject to a terminal disclaimer.

(21) Appl. No.: 16/432,473

(22) Filed: Jun. 5, 2019

(65) Prior Publication Data

US 2019/0368997 A1    Dec. 5, 2019

Related U.S. Application Data

(60) Provisional application No. 62/680,812, filed on Jun. 5, 2018.

(51) Int. Cl.
| | |
|---|---|
| *G01N 15/08* | (2006.01) |
| *E21B 49/02* | (2006.01) |
| *G01N 33/24* | (2006.01) |

(52) U.S. Cl.
CPC ......... *G01N 15/0826* (2013.01); *E21B 49/02* (2013.01); *G01N 33/24* (2013.01)

(58) Field of Classification Search
CPC ..... G01N 15/0825; G01N 33/24; E21B 49/02
See application file for complete search history.

(56) References Cited

U.S. PATENT DOCUMENTS

| 8,924,029 B2 * | 12/2014 | Nath ...................... E21B 43/26 |
| | | 700/282 |
| 9,709,477 B2 * | 7/2017 | Chertov ............. G01N 15/0826 |
| 9,709,478 B2 * | 7/2017 | Chertov ............. G01N 15/0826 |
| 9,746,410 B2 * | 8/2017 | Chertov .................. G01N 7/00 |

(Continued)

OTHER PUBLICATIONS

Russian et al., "Multi-Continuum Approach to Modeling Shale Gas Extraction," Springer Science and Business Media LLC, 23 pages (Year: 2015).*

(Continued)

*Primary Examiner* — John Fitzgerald
(74) *Attorney, Agent, or Firm* — Bracewell LLP; Constance G. Rhebergen; Vivek P. Shankam

(57) ABSTRACT

Systems and methods for analyzing and modeling natural gas flow in subterranean shale reservoirs. In some embodiments, methodologies and techniques for determining and modeling natural gas flow in shale formations using methodologies and techniques capable of determining natural gas properties related to dual-continuum flow, permeability, and pressure within a subterranean shale reservoir. In some embodiments, the natural gas properties are determined by subjecting a subterranean shale reservoir sample to pulse-decay analysis. In certain embodiments, the methodologies and techniques described may be used in various reservoirs exhibiting macroporosity and microporosity, such as fractured reservoirs and carbonate reservoirs composed of reservoir fluids.

8 Claims, 7 Drawing Sheets

(56) References Cited

U.S. PATENT DOCUMENTS

| | | | |
|---|---|---|---|
| 9,927,344 B2* | 3/2018 | Chertov | G01N 7/00 |
| 9,989,512 B2 | 6/2018 | Haggerty | |
| 10,302,543 B2* | 5/2019 | Hannon, Jr. | G01N 1/28 |
| 10,401,274 B2* | 9/2019 | Liu | G01N 33/24 |
| 10,416,064 B2* | 9/2019 | Chen | E21B 49/08 |
| 10,436,696 B2* | 10/2019 | Liu | G01N 33/24 |
| 10,502,673 B2* | 12/2019 | Chertov | G01N 15/088 |
| 10,571,384 B2* | 2/2020 | Liu | G01N 33/24 |
| 10,591,399 B2* | 3/2020 | Liu | G01N 15/0826 |
| 2005/0165593 A1* | 7/2005 | Lenormand | E21B 49/00 703/10 |
| 2012/0215365 A1* | 8/2012 | Nath | E21B 43/26 700/282 |
| 2013/0054157 A1 | 2/2013 | Lasseux et al. | |
| 2015/0293007 A1 | 10/2015 | Ramakrishnan et al. | |
| 2015/0293008 A1 | 10/2015 | Ramakrishnan et al. | |
| 2015/0362419 A1* | 12/2015 | Chertov | G01N 15/0806 73/38 |
| 2015/0369718 A1* | 12/2015 | Chertov | G01N 15/0806 73/38 |
| 2015/0369719 A1* | 12/2015 | Chertov | G01N 15/082 73/38 |
| 2016/0041079 A1* | 2/2016 | Chertov | G01N 15/082 73/38 |
| 2016/0334322 A1 | 11/2016 | Ramakrishnan et al. | |
| 2017/0016812 A1* | 1/2017 | Liu | G01N 15/0826 |
| 2017/0167964 A1* | 6/2017 | Liu | G01N 33/24 |
| 2018/0209889 A1* | 7/2018 | Chertov | G01N 7/00 |
| 2018/0340878 A1* | 11/2018 | Liu | G01N 33/24 |
| 2018/0348111 A1 | 12/2018 | Hannon | |
| 2018/0364142 A1 | 12/2018 | Georgi et al. | |
| 2019/0234859 A1* | 8/2019 | Chen | E21B 49/08 |
| 2019/0250091 A1* | 8/2019 | Liu | G01N 15/0826 |
| 2020/0363310 A1* | 11/2020 | Zhang | E21B 49/088 |
| 2020/0370989 A1* | 11/2020 | Zhang | G01N 15/0806 |
| 2020/0386664 A1* | 12/2020 | Zhang | G01N 33/24 |

OTHER PUBLICATIONS

Liu et al., "A criterion for evaluating the effect of shale-matrix dual-continuum flow on gas production," Geomech. Geophys. Geoenerg 5:87-102 (Year: 2019).*

Feng, "An optimized transient technique and flow modeling for laboratory permeability measurements of unconventional gas reservoirs with tight structure.", Journal of Natural Gas Science and Engineering, 2017, pp. 603-614, Elsevier.

International Search Report and Written Opinion for related PCT application PCT/US2019/035179 dated Sep. 10, 2019.

Darabi, Hamed et al.; "Gas flow in ultra-tight shale strata" Journal of Fluid Mechanics, vol. 710, Nov. 2012, pp. 641-685.

Dicker, A.I. et al.; "A Practical Approach for Determining Permeability From Laboratory Pressure-Pulse Decay Measurements" SPE 17578, SPE International Meeting on Petroleum Engineering; Tianjin, China, Nov. 1-4, 1988; pp. 285-292.

Han, Guofeng et al.; "Analysis method of pulse decay tests for dual-porosity cores" Journal of Natural Gas Science and Engineering 59 (2018); pp. 274-286.

Jones, S.C.; "A Technique for Faster Pulse-Decay Permeability Measurements in Tight Rocks" SPE 28450, SPE Annual Technical Conference & Exhibition, Sep. 25-28, 1994; pp. 19-25.

Liu, Hui-Hai et al.; "An Innovative Laboratory Method To Measure Pore-Pressure-Dependent Gas Permeability of Shale: Theory and Numerical Experiments" SPE 191123, 2018 SPE Reservoir Evaluation & Engineering; pp. 1-10.

Liu, Hui-Hai et al.; "Pressure pulse-decay tests in a dual-continuum medium: Late-time behavior" Journal of Petroleum Science and Engineering 147 (2016) pp. 292-301.

Singh, H. et al.; "Nonempirical Apparent Permeability of Shale" SPE 170243, Aug. 2014 SPE Reservoir Evaluation & Engineering; pp. 414-424.

Singh, Harpreet; "Integration of Nonempirical Shale Permeability Model in a Dual-Continuum Reservoir Simulator" SPE 167125, SPE Unconventional Resouices Conference—Canada, Nov. 5-7, 2013; pp. 1-11.

* cited by examiner

SYSTEMS AND METHODS FOR ANALYZING NATURAL GAS FLOW IN SUBTERRANEAN RESERVOIRS

CROSS REFERENCE TO RELATED APPLICATIONS

This application claims priority from U.S. Provisional Application No. 62/680,812, filed Jun. 5, 2018, and titled "SYSTEMS AND METHODS FOR ANALYZING NATURAL GAS FLOW IN SUBTERRANEAN FORMATIONS," the entire contents of which is incorporated by reference.

BACKGROUND

1. Technical Field

This disclosure relates generally to systems and methods for analyzing and modeling natural gas flow in subterranean reservoirs.

2. Description of Related Art

The increasing energy demands of the global economy require the identification of new hydrocarbon reservoirs as well as the maximization of hydrocarbon recovery from existing reservoirs. The identification and recovery of the vast deposits of hydrocarbons trapped within subterranean reservoir formations have long been recognized as a challenge to the industry. The accurate identification and characterization of shale gas flow is critical for assessing and maximizing shale gas recovery in challenging environments such as tight shale formations (in which the matrix pore network is composed of nanometer to micrometer size pores) comprising shale gas enriched with organic based material.

The use of pulse-decay permeability (PDP) measurements for the characterization and modeling of subterranean shale gas flow has previously been described, for example, in Jones, "A Technique for Fast Pulse-Decay Permeability Measurements in Tight Rocks," SPEFE (March 1997) 19-25; Darabi et al., "Gas Flow in Ultra-Tight Shale Strata," Journal of Fluid Mechanics 710, 641-658 (2012) and Dicker et al., "A Practical Approach for Determining Permeability from Laboratory Pressure-Pulse Decay Measurements," 1988 SPE International Meeting on Petroleum Engineering (Paper SPE 17578).

SUMMARY

However, these methodologies and techniques have well defined limitations in shale gas identification and analysis, particularly with regard to the characterization and modeling of shale gas flow within the numerous types of pore systems that can exist in a reservoir, including "fast-flow" and "slow-flow" pathways. The need therefore exists for improved methods and techniques for assessing subterranean shale gas reservoirs and deposits for enhancing natural gas recovery.

Some prior experiments took advantage of the pulse-decay permeability (PDP) measurements and used the pressure transient data to characterize the dual-continuum behavior of the source rock formation. These experiments introduced the mass transfer coefficient between the two continua for the matrix, and developed an analytical technique to determine the apparent mass transfer coefficient using the PDP measurements. However, these methods are limited to the use of the same volume of the upstream and downstream reservoirs in the PDP setup. It is more desirable to use different volumes for the two reservoirs to reduce the experimental time.

As a further improvement, some embodiments in the present disclosure provide a new approach to estimate the mass transfer coefficient from the PDP measurements associated with different volumes of the upstream and downstream reservoirs. Example embodiments include the methodology and analysis workflow to identify the dual-continuum behavior and to estimate the apparent mass transfer coefficient between the two continua. In some embodiments, methodologies and techniques for determining and modeling natural gas flow in shale formations capable of determining natural gas properties related to permeability and dual-continuum flow within a subterranean reservoir are provided. In further embodiments, the natural gas properties are determined by subjecting a subterranean reservoir sample to pulse-decay analysis. In certain embodiments, the methodologies and techniques described here can be used in various reservoirs exhibiting both macroporosity and microporosity, such as shale gas reservoirs, fractured reservoirs, and carbonate reservoirs composed of reservoir fluids.

Accordingly, one example embodiment is a method of determining a flow characteristic of a subterranean reservoir formation for the purpose of predicting production capabilities. The method includes obtaining a reservoir sample from the subterranean reservoir formation, creating a pressure pulse in upstream reservoir, obtaining from the reservoir sample dual-continuum test data, determining a mass transfer coefficient from the dual-continuum test data, and determining the flow characteristic from the mass transfer coefficient. The method may also include generating single-continuum test data if dual-continuum behavior is absent.

Another example embodiment is a method of obtaining dual-continuum test data including the steps of placing a reservoir sample in a sample holder, where the sample is fluidly connected to an upstream gas reservoir and a downstream gas reservoir, filling the upstream gas reservoir, the downstream gas reservoir, and the sample with a gas to a gas pressure such that the gas pressure in the upstream gas reservoir, the downstream gas reservoir and the sample is uniform, closing an upstream valve, where closing the upstream valve isolates the upstream gas reservoir from both the downstream gas reservoir and the sample, imposing a pulse pressure in the upstream gas reservoir to initiate the test, opening the upstream valve generally at the same time the pulse pressure is transported from the upstream reservoir to the downstream reservoir by passing through the sample, and measuring the dual-continuum test data.

Another example embodiment is a system to measure dual-continuum test data. The system includes a sample holder, the sample holder configured to secure a reservoir sample, an upstream gas reservoir fluidly connected to the sample and a downstream gas reservoir, a downstream gas reservoir fluidly connected to the sample and the upstream gas reservoir, an upstream valve, the upstream valve configured to isolate the upstream gas reservoir from both the sample and the downstream gas reservoir, and a downstream valve, the downstream valve configured to isolate the downstream gas reservoir from both the sample and the upstream gas reservoir.

BRIEF DESCRIPTION OF DRAWINGS

The foregoing aspects, features, and advantages of embodiments of the present disclosure will further be appreciated when considered with reference to the following description of embodiments and accompanying drawings. In describing embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

For simplicity and clarity of illustration, the figures illustrate the general manner of construction, and descriptions and details of well-known features and techniques may be omitted to avoid unnecessarily obscuring the discussion of the described embodiments. Additionally, elements in the drawing figures are not necessarily drawn to scale. For example, the dimensions of some of the elements in the figures may be exaggerated relative to other elements to help improve understanding of embodiments of the example embodiment. Like reference numerals refer to like elements throughout the specification.

DETAILED DESCRIPTION

The methods and systems of the present disclosure will now be described more fully with reference to the accompanying drawings in which embodiments are shown. The methods and systems of the present disclosure may be in many different forms and should not be construed as limited to the illustrated embodiments set forth here; rather, these embodiments are provided so that this disclosure will be thorough and complete, and will fully convey its scope to those skilled in the art.

Figure 1:
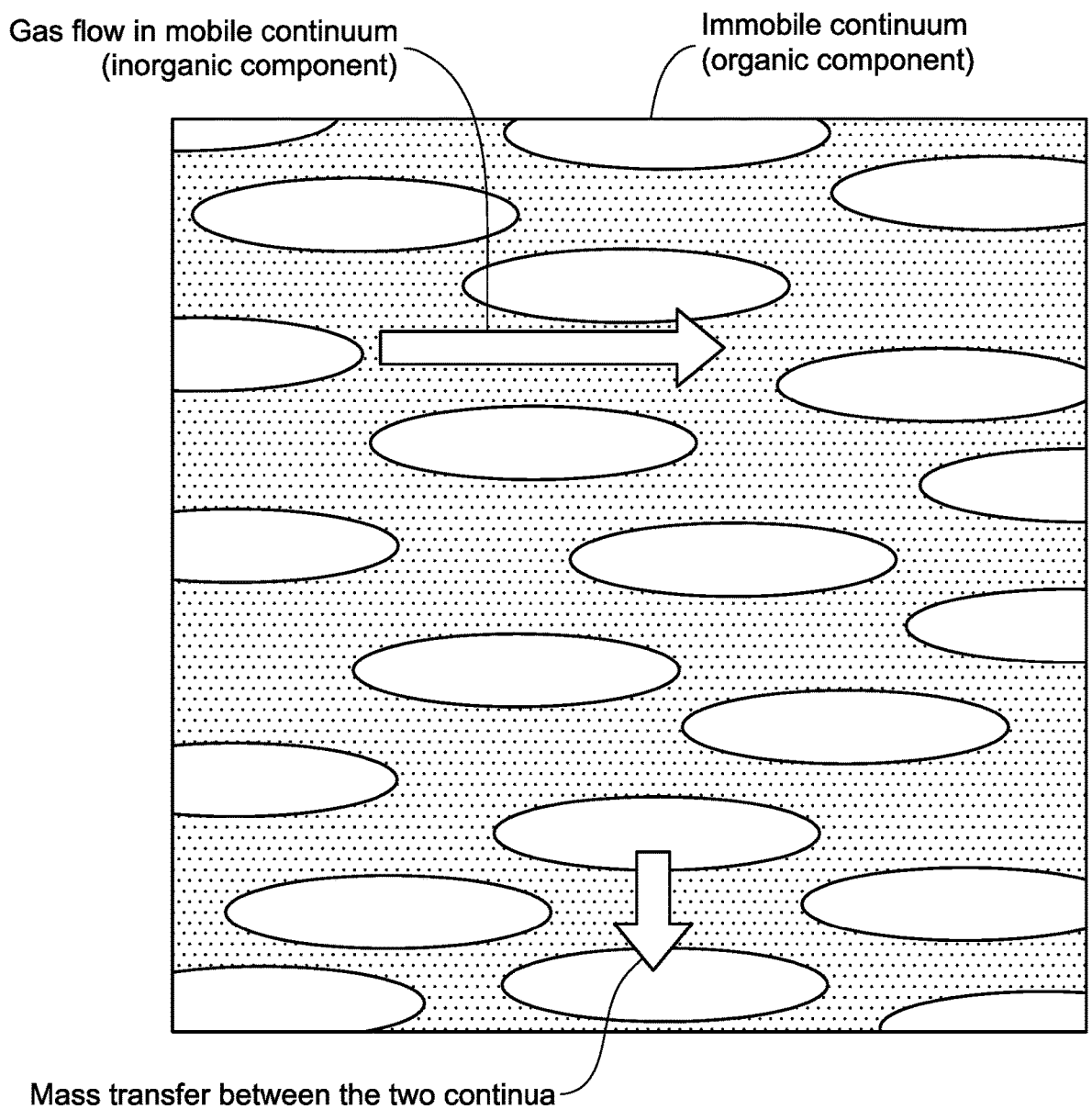
FIG. 1 shows a schematic of material transfer, for example a gas mass transfer, within a subterranean shale formation, according to one or more example embodiments.

FIG. 1 illustrates flow behavior in a dual-continuum shale matrix. Dual-continuum is characterized by the properties of an organic material continuous phase (first continuum component) and the properties of an inorganic material continuous phase (second continuum component) of a subterranean reservoir. Within the context of the example embodiment, the mobile continuum corresponds to the inorganic component of the shale matrix while the immobile continuum corresponds to the organic component of the shale matrix. In some embodiments, dual-continuum properties are associated with one or more subterranean shale matrices and their fluid properties, such as fast-flow pathways and slow-flow pathways within the shale matrix, their pore size properties including pore size distribution, and physicochemical differences between the organic material component and inorganic material component of the shale formation.

The terms "organic material", "organic component" and "organic" refer to carbonaceous materials or substrates derived from a hydrocarbon based source or sources having a low permeability. As used in this disclosure, the term "low permeability" is a relative term that refers to the difference in permeability between the organic component and inorganic component, with the organic component having the lower permeability. While in no way limiting the scope of the example embodiment, an organic material or organic component can include one or more of pre-bitumen bituminous groundmass such as the remains of woody and non-woody plants and their organic components; animals, non-animal organisms and cellular debris. An organic material or organic component, in accordance with the example embodiment, can be volatile or non-volatile. The organic material does not include the hydrocarbon targeted for removal from the formation.

As used in this disclosure, the terms "inorganic material", "inorganic component" and "inorganic" refer to non-hydrocarbon containing materials or substrates having a high permeability. As used in this disclosure, the term "high permeability" is a relative term that refers to the difference in permeability between the organic component and inorganic component, with the organic component having the higher permeability. In accordance with the example embodiment, an inorganic material or component includes but is not limited to one or more transition metals including cadmium, cobalt, chromium, mercury, nickel, iron, copper, vanadium, uranium, and barium; non-transition metals such as sulfur, nitrogen and arsenic; minerals such as quartz, calcite and dolomite; and the non-carbonaceous components of coke or semi-coke.

As used in this disclosure, the term "mobile continuum" refers to the globally permeable continuum of the dual-continuum system. The mobile continuum corresponds to the inorganic component of a shale matrix.

As used in this disclosure, the term "immobile continuum" refers to the continuum that is not globally connected or has negligible global permeability in the dual-continuum system. The immobile continuum refers to the organic component of a shale matrix. The immobile continuum can be mobile for gas transport to the mobile continuum.

As used in this disclosure, the term "fast-flow pathways" refers to global permeable flow paths corresponding to high permeability in a rock sample.

As used in this disclosure, the term "slow-flow pathways" refers to the flow paths corresponding to low permeability in a rock sample.

As used in this disclosure, the term "confining pressure" or "confining stress" refers to the pressure or physical stress imposed on a rock sample.

As used in this disclosure, the terms "late-time stage" or "late-term stage" refers to the point in the dual-continuum test when any difference in the pressure among the upstream gas reservoir and downstream gas reservoir and the mobile continuum is relatively small. As used in this disclosure, "relatively small" refers to the condition that a pressure variation has a negligible impact on gas properties, such as density. One technique for analyzing pulse-decay data uses only late-term stage measurements, which requires only the first root of an otherwise infinite series to calculate permeability. The late-time stage can occur between one (1) millisecond (ms) to about one (1) week after the pressure-transient portion of the dual-continuum test is initiated.

As used in this disclosure, "uniform gas pressure" refers to the pressure in the pulse-decay system being the same throughout the pulse-decay system. When the pulse-decay system is at a uniform gas pressure, the pressure in the upstream reservoir, the downstream reservoir, and the sample are the same value. Achieving uniform gas pressure can take between about 1 minute and about 5 hours, alternately less than 1 hour, alternately less than 5 hours, alternately between about 1 hour and about 5 hours, and alternately between about 2 hours and about 4 hours.

The example embodiment addresses problems associated with the identification, analysis and recovery of shale gas from a shale matrix. The shale matrix can exhibit dual-continuum gas-flow behavior owing to property differences between the organic components and inorganic components in the shale matrix. In some embodiments, a reservoir sample evaluated using the example embodiment can be treated as a dual-continuum system for determining properties of the reservoir sample, such as mass transfer properties of shale, including fast-flow pathways and slow-flow pathways within one or more samples of interest. The example embodiment advantageously provides a method to estimate the mass transfer coefficient between the dual-continuum with pulse-decay. The method of the example embodiment allows determination of mass transfer coefficient in porous media with pulse-decay.

The example embodiment advantageously provides for methodologies and techniques for determining an effective mass transfer coefficient of a reservoir sample based on dual-continuum characteristics from pulse-decay test data.

Example embodiments provide methods and techniques for determining values of parameters describing gas flow in a dual-continuum shale matrix. The example embodiment provides a method to determine the mass transfer coefficient for gas flow in a dual-continuum matrix of a tight organic-rich shale (in which the matrix pore network is composed of nanometer to micrometer size pores). The example embodiment provides a method to identify dual-continuum characteristics from pulse-decay test data and to estimate a mass transfer coefficient between the two continua if the dual-continuum characteristic exists. The methods of the example embodiment use pulse-decay data.

As used in this disclosure, the term "mass transfer coefficient" refers to the mass flow rate between the two continua divided by the gas pressure difference between the two continua per unit bulk volume of shale matrix. The mass transfer coefficient is a key parameter for describing mass transfer between the two continua.

As used in this disclosure, the term "shale gas" refers to natural gas or a natural gas deposit located adjacent to or within a subterranean shale formation. Within the context of the example embodiment, shale gas can be identified and recovered from active hydrocarbon drilling and recovery processes such as horizontal drilling, hydraulic fracturing, chemical fracturing, such as slick water fracturing, or a combination of recovery processes. Shale gas can include methane, ethane, propane, butane, carbon monoxide, carbon dioxide, and combinations thereof.

The term "pulse-decay test," alternatively known as the "transient pulse method," refers to a technique for measuring the permeability of a material.

Figure 2:
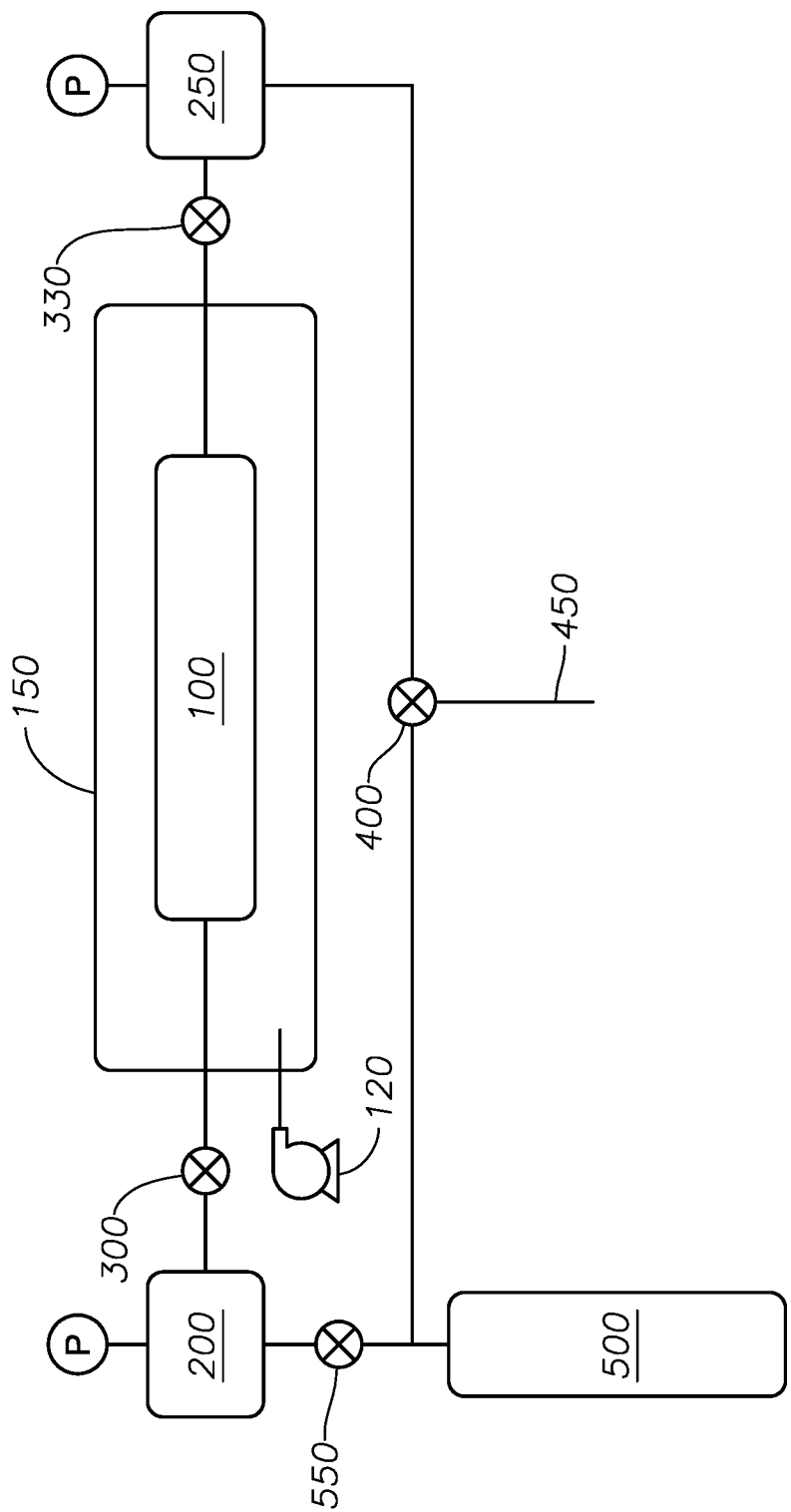
FIG. 2 shows a pulse-decay system for gathering dual-continuum test data, according to one or more example embodiments.

A dual-continuum test uses a pulse-decay system as shown in FIG. 2. Rock sample 100 is placed in holder 150. Holder 150 can apply hydrostatic confining stress to rock sample 100. Rock sample 100 is a cylindrical sample from a reservoir formation. Rock sample 100 is fluidly connected to both upstream reservoir 200 and downstream reservoir 250. At the start of the pulse-decay test, the pulse-decay system is in equilibrium with a uniform gas pressure. Uniform gas pressure can be achieved by filling upstream reservoir 200, downstream reservoir 250, and holder 150 with a gas to a gas pressure. In at least one embodiment, the gas flows from gas reservoir 500 to fill upstream reservoir 200 and downstream reservoir 250. Examples of gases that can be used to fill the pulse-decay system include nitrogen, carbon dioxide, helium, and argon. The gas pressure can be between about 1 psi (pounds per square inch) and about 10,000 psi, alternately between about 1000 psi and about 5000 psi, alternately between 1000 psi and 2000 psi. The pulse-decay system is allowed to stabilize at which point the gas pressure is a uniform gas pressure. After a uniform gas pressure is reached, valve 300 is closed, closing off the connection between upstream reservoir 200 and rock sample 100. The pressure in upstream reservoir 200 is then increased by a pressure-increase. The pressure-increase is caused by adding more gas from gas reservoir 500. In at least one embodiment, the pressure-increase is 10 psi. In at least one embodiment, the pressure-increase is at least 10 psi. When the pressure in upstream reservoir 200 becomes constant at the pressure-increase greater than the uniform gas pressure, gas reservoir valve 330 is closed and valve 300 is opened which initiates the pressure-transient portion of the measurement. Opening valve 300 introduces a pressure pulse from upstream reservoir 200 due to the pressure in upstream reservoir 200 being greater than the pressure in the rest of the pulse-decay system. The pressure in upstream reservoir 200 and the pressure in downstream reservoir 250 are measured and recorded as a function of time (the "pulse-decay test data"). The pressure in upstream reservoir 200 declines with time as the pressure pulse travels through rock sample 100. The step-function pressure pulse gradually becomes a smooth pressure gradient. Pressure in downstream reservoir 250 remains constant until the smoothed pressure pulse reaches the downstream end of rock sample 100, at which time pressure in downstream reservoir 250 increases. A pulse-decay test ends when the pressure in upstream reservoir 200 is nearly equal to the pressure in downstream reservoir 250 and the pressure in both stabilizes. As used here, "nearly equal to" means that the pressure in upstream reservoir 200 and the pressure in downstream reservoir 250 differ by a value less than the measurement error range. Confining pump 120 can provide a confining pressure on rock sample 100 in holder 150. Three-way valve 400 can be used to control gas flow between upstream reservoir 200, downstream reservoir 250 and vent line 450. Three-way valve is a three-way valve that allows flow to be adjusted in multiple lines. Vent line 450 can be used to release the gas from the pulse-decay system. In accordance with the example embodiment, pulse-decay can be used to measure the permeability of shale rock. In preferred embodiments, pulse-decay is used to determine shale rock properties related to gas flow in a shale rock matrix, including dual-continuum gas flow.

As used in this disclosure, "stabilize" or "steady state" or "equilibrate" refers to a state where the pressure in the pulse-decay system does not change with time. The pressure in each unit of the pulse-decay system remains constant and the entire pulse-decay system equilibrates. The pressure can take between about 30 minutes and about 10 hours to stabilize.

As used in this disclosure, the term "dual-continuum" refers to a dual-porosity system having one globally permeable continuum and a second that is either not globally connected or has negligible global permeability. A continuum in a subsurface material refers to a subdomain or feature, for example a feature can be a fracture network, that has similar flow and transport properties; these properties, however, are dramatically different from those in other subdomains or features within the same material.

A first method for estimating the mass transfer coefficient is now described with reference to FIG. 2. In some embodiments, the methodologies and techniques described in this disclosure assume that a subterranean shale reservoir sample can be characterized as a dual-continuum system that exhibits gas flow pathways, including both fast-flow pathways and slow-flow pathways and further exhibits negligible global permeability of slow-flow pathways and can therefore be characterized with respect to mass transfer processes as depicted in FIG. 1. As will be shown, because the pressure difference between upstream reservoir 200 and downstream reservoir 250 is an exponential function of time with permeability as a parameter, permeability can be based on the slope from the plot of log of the pressure difference versus time, allowing the estimation of permeability from the data generated by the pulse-decay system.

The PDP measurement is a technique to measure the permeability of the tight organic-rich shale samples. Current applications for the PDP measurement almost exclusively treat a test sample as a single-continuum system. A dual-continuum sample that involves more complex flow properties than a single-continuum sample is discussed here. Some previous studies developed an analytical solution to analyze the late-time PDP measurement data for dual-continuum rock matrix, and provided an analytical technique to identify the dual-continuum behavior and to estimate the apparent mass transfer coefficient between the two continua. However, these studies were only designed for PDP setups with the same volume of the upstream and downstream reservoirs. Example embodiments disclosed here provide a new technique to characterize the dual-continuum behavior of a test sample with different upstream and downstream reservoir volumes in the PDP setups.

Referring to FIG. 2, a pulse-decay test system according to the example embodiment is provided. Reservoir sample 100 is placed in sample holder 150. Reservoir sample 100 can be isolated from any subterranean reservoir formation about which information is desired. The subterranean reservoir formations can include limestone, sandstone, and shale. In at least one embodiment, reservoir sample 100 can be a cylinder having a length and a diameter. In at least one embodiment, the length of reservoir sample 100 is in a range of between about 0.1 inches to about 16 inches. In at least one embodiment, the diameter is in the range of between about 0.1 inches to about 4 inches. In at least one embodiment, the length is smaller than the diameter. At the start of the dual-continuum test, the dual-continuum test system is in equilibrium with a uniform gas pressure. Uniform gas pressure can be achieved by filling upstream gas reservoir 200, downstream gas reservoir 250, and reservoir sample 100 with a gas to a gas pressure. Examples of gases that can be used to fill the dual-continuum test system include carbon dioxide, helium, and argon. The gas pressure can be between about 1000 psi and about 10,000 psi, alternately between about 2,000 psi and 8,000 psi, and alternately between about 4,000 psi and 6,000 psi. In at least one embodiment, the gas pressure is 5,000 psi. The dual-continuum test system is allowed to stabilize at which point the gas pressure is at a uniform gas pressure. After a uniform gas pressure is reached, upstream valve 300 is closed, closing off the connection between upstream gas reservoir 200 and reservoir sample 100. The pressure in upstream gas reservoir 200 is adjusted to an adjusted pressure, where the adjusted pressure can be greater than or less than the uniform gas pressure. The absolute difference between the uniform gas pressure and the adjusted pressure can be from between about 10 psi to 1000 psi. In at least one embodiment, the pressure in upstream gas reservoir 200 is adjusted by adding additional gas from reservoir 500 through gas valve 550, such that the adjusted pressure is greater than the uniform gas pressure. In at least one embodiment, the pressure in upstream gas reservoir 200 and downstream gas reservoir 250 are adjusted by venting gas from the system using vent valve 400, which can be used to vent gas through vent 450, such that the adjusted pressure is less than the uniform gas pressure. The pressure in upstream gas reservoir 200 and the pressure in downstream gas reservoir 250 are allowed to stabilize at the adjusted pressure. To begin the dual-continuum test, initially the upstream valve 300 is opened. Opening upstream valve 300 initiates the pressure-transient portion of the measurement by introducing pressure pulses from upstream gas reservoir 200. Opening upstream valve 300 introduces a pressure pulse from upstream gas reservoir 200 due to the pressure in upstream gas reservoir 200 being different than the pressure in reservoir sample 100. The pressure in upstream gas reservoir 200, the pressure in downstream gas reservoir 250, or the pressure in both upstream gas reservoir 200 and downstream gas reservoir 250 are measured and recorded as a function of time (the "dual-continuum test data"). The pressure in sample holder 150 can be controlled by the confining pump 120. The dual-continuum test ends when the pressure in upstream gas reservoir 200 and in downstream gas reservoir 250 stabilizes. The dual-continuum test data is analyzed according to methods of the example embodiment to estimate a mass transfer coefficient.

Advantageously, the pulse-decay test system of the example embodiment, as shown in FIG. 2, removes the constraint that the gas flows from the upstream gas reservoir to the downstream gas reservoir through the reservoir sample. By doing so, the dual-continuum test can reduce the time to reach the late-time stage in the dual-continuum test system. When the late-time stage occurs earlier, the pressure differences observed can be attributed to the pressure differences in the two continua, which translates to the dual-continuum test data exhibiting stronger gas pressure signals corresponding to the flow behavior of a dual-continuum matrix. Advantageously, the dual-continuum test provides a method for increased accuracy of estimating the mass transfer coefficient in a shale matrix reservoir.

A dual-continuum system includes two continua: the mobile continuum (that is the globally permeable continuum) and the immobile continuum that only transports gas between itself to the mobile continuum (that is it has negligible global permeability or is not globally connected). The mass transfer coefficient is defined as the mass flow rate between these two continua (for example organic and inorganic components of the shale samples) divided by the gas pressure difference between them per unit bulk volume. According to prior studies, a transport parameter ($B^*$, that will be used to define the transfer coefficient) can be given as:

$$B^* = \frac{\partial \rho_{m,i}}{\partial t} \bigg/ (p_m - p_i) \quad (1)$$

where m and i represents the mobile and immobile continua respectively, $P_m$ and $P_i$ represent the gas pressure in the mobile and immobile continua, and $\rho_{m,i}$ is the transfer mass between two continua per unit bulk volume of the porous media.

FIG. 1 shows the gas flow behavior in a dual-continua system. This dual-continuum system includes only one globally connected permeable continuum, which is the mobile continuum. The immobile continuum only transfers gas to the mobile continuum. Then, the apparent mass transfer coefficient (B) is defined as:

$$B = B^* \bigg/ \left(\frac{d\rho_{m,i}}{dp_i}\right) \quad (2)$$

The units of B* and B are $L^{-2}T^{-1}$ and $T^{-1}$ (L and T represent the length and time), respectively. The coefficient B can be treated as a measure for the ability of gas transfer between the two continua. A smaller value of B indicates a stronger dual-continuum behavior (that is a weaker gas transfer ability between two continua) since it takes longer time for gas to reach the equilibrium pressure between the two continua. Therefore, the apparent transfer coefficient B is an important factor to characterize the dual-continuum behavior. In the following section, a new method to estimate the B factor for the dual-continuum samples is disclosed.

Figure 3:
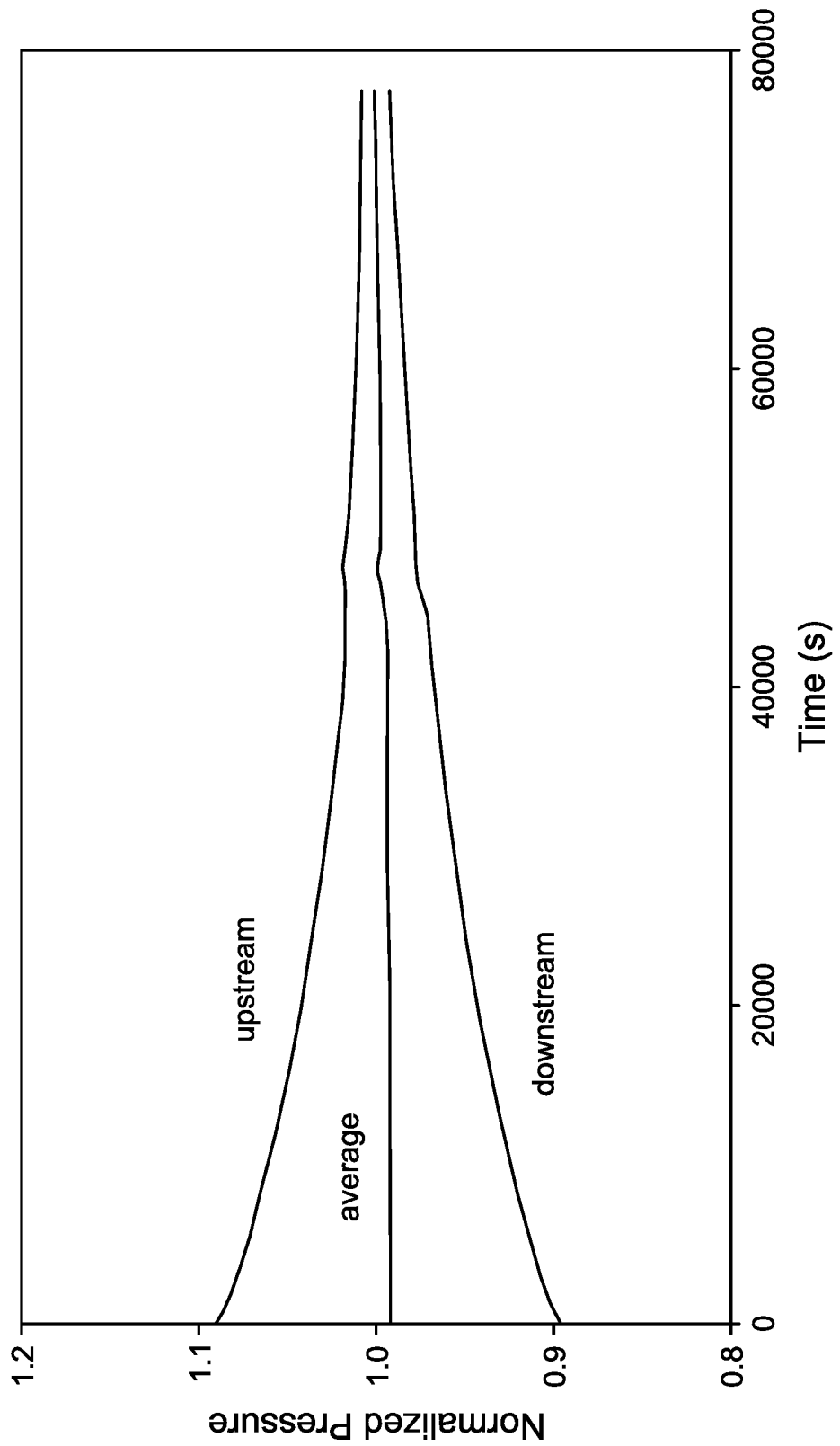
FIG. 3 shows a graphical representation of normalized shale gas pressure for an upstream reservoir, a downstream reservoir and an average of the upstream and downstream reservoirs as a function of time in accordance with some embodiments.

FIG. 3 shows measurements for the black shale sample in terms of normalized pressure. Due to test issues related to confining stress control at about 50,000 seconds (s), pressure change is not smooth near that time. However, the late-time stage behavior is not impacted after that time. The method according to one example embodiment uses the pressure transient data from the PDP measurement to check the presence of the dual-continuum behavior. The PDP measurement consists of upstream and downstream reservoirs and a sample holder.

Figure 4:
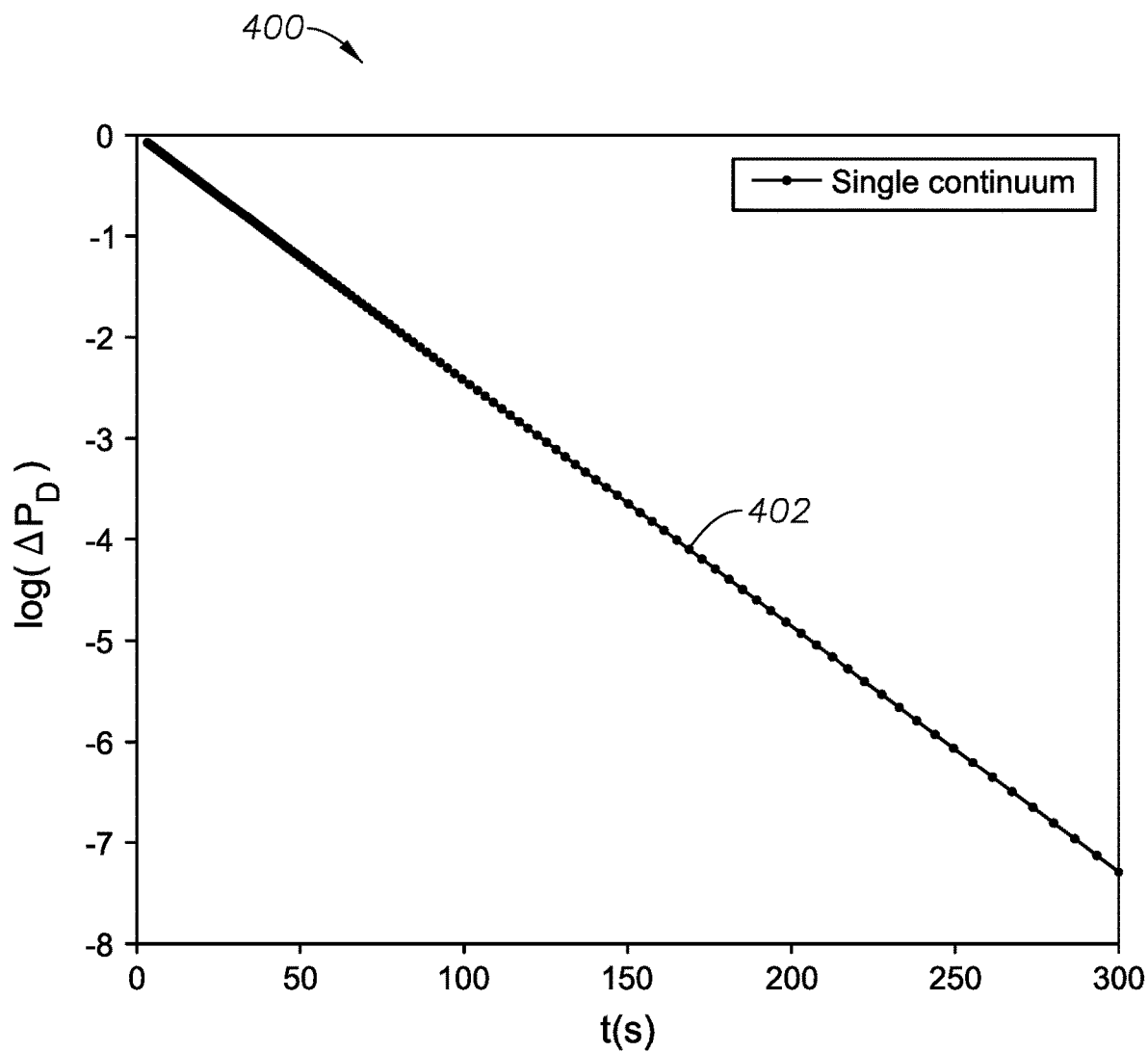
FIG. 4 is a line graph showing a linear relation of log of the pressure difference between the upstream and downstream reservoirs versus time for a single continuum test sample, according to one or more example embodiments.

FIG. 4 shows the schematic graph 400 of the results obtained from the PDP measurement setup. Initially, both the upstream and downstream valves keep open until the whole system reaches a uniform gas pressure. Next, the upstream valve is closed and a small pulse pressure (of about 10 psi) is imposed in the upstream reservoir. Finally, the upstream valve is open and the gas flows through the upstream reservoir to the downstream reservoir by passing through the core sample. The upstream reservoir pressure decreases and downstream reservoir pressure increases, and both the pressures are recorded as a function of time.

One example embodiment provides an analytical technique to check the dual-continuum behavior and to estimate the apparent mass transfer coefficient B through analysis of the pressure transient data from PDP measurement. To check the dual-continuum behavior, first the log of the pressure difference between the upstream and downstream reservoirs is plotted against time. It is a single continuum system if the curve is a straight line 402 (see FIG. 4). However, if the curve bends up at a later time (linear relation breaks up), the single-continuum assumption is not valid. It is then determined whether the test sample exhibits the dual-continuum behavior or not. FIG. 4 is a line graph 400 showing a linear relation 402 of log of the pressure difference between the upstream and downstream reservoirs versus time for a single continuum test sample, according to one or more example embodiments.

Figure 5:
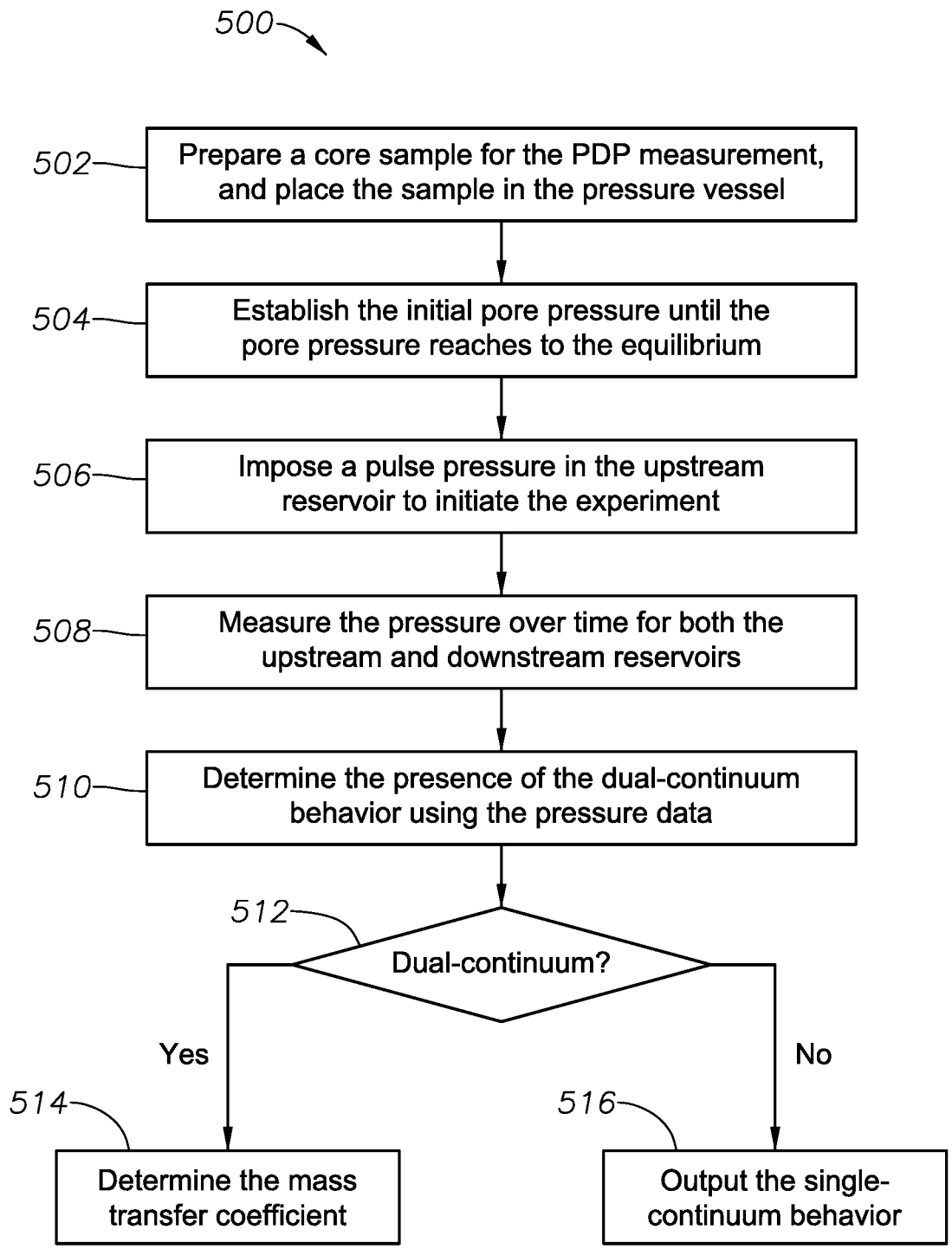
FIG. 5 is a flow diagram illustrating example steps in a method for characterizing the dual continuum behavior and estimating the apparent mass transfer coefficient 'B' between the two continua through PDP measurements, according to one or more example embodiments.

FIG. 5 is a flow diagram illustrating example steps in a method 500 for characterizing the dual continuum behavior and estimating the apparent mass transfer coefficient B between the two continua through PDP measurements, according to one or more example embodiments. In this section, a workflow that can be used to check the dual-continuum behavior and to estimate the apparent mass transfer coefficient B between the two continua through the PDP measurement, as shown in FIG. 5, is discussed. At step 502, a core sample is first prepared and the sample is placed in the PDP pressure vessel. At step 504, the initial pore pressure is established until the pore pressure reaches equilibrium. At step 506, a pulse pressure in the upstream reservoir is imposed to initiate the experiment. At step 508, the pressure is measured over time for both the upstream and down reservoirs. Then a PDP measurement is carried out on this prepared sample. Next, at step 510 the pressure transient data for both the upstream and downstream reservoirs are recorded and analyzed to check the dual-continuum behavior by using the aforementioned technology. If it exhibits the dual-continuum behavior, at step 512, then the pressure transient data are used to estimate the mass transfer coefficient in step 514. However, if it is determined that there is no dual-continuum at step 512, then the system generates and outputs the single continuum behavior data at step 516. This work flow is user-friendly and can be used as a routine in practice with the following non-limiting benefits: 1) it uses the widely-used PDP measurement; 2) the procedure to check the dual-continuum behavior is straight forward since it only needs to check the linearity of curves; 3) the apparent mass transfer coefficient for the dual-continuum system can be easily estimated from the slop of the linear curve.

The derivation of the analytical solution with respect to the gas flow in a dual-continuum system for the PDP measurement is explained in the following paragraphs. Based on this analytical solution, an analytical technique to determine the apparent mass transfer coefficient of a dual-continuum system with different volumes of upstream and downstream reservoirs can be derived. To start with $\Delta p_D$, $p_u$, $p_d$, $\Delta p_{pulse}$, k, $A_r$, $\mu$, L, $V_u$, $V_d$, $V_p$ and $c_g$ are denoted as the normalized pressure difference between the upstream and downstream reservoirs, the upstream reservoir pressure, the downstream reservoir pressure, the pressure pulse, the permeability of the rock sample, the cross-section area of the rock sample, the gas viscosity, the length of the rock sample, the volume of the upstream reservoir, the volume of the downstream reservoir, pore volume and the gas compressibility, respectively.

To characterize the dual continuum behavior and estimate the apparent mass transform coefficient B, the pressure transient data from the pulse-decay measurement are analyzed using the following equation:

$$\ln(F(t)\Delta p_D) = -Bt + C_3 \quad (3)$$

where $C_3$ is a constant and $$\Delta p_D = \frac{p_u - p_d}{\Delta p_{pulse}} \quad (4)$$

$$F(t) = \frac{d(\ln(p_u - p_d))}{dt} - \frac{kA_r}{\mu L V_d c_g} \frac{(\eta + 1) - 3}{1 + \frac{b}{6}(\eta + 1)} \quad (5)$$

Parameters, η and b from Eq. (3) are defined as:

$$\eta = \frac{(V_u - V_d)}{\frac{V_p}{2} + V_d} \quad (6)$$

$$b = \frac{V_p}{V_d} \quad (7)$$

Eq. (3) is valid for a dual-continuum test sample and the detailed derivation is given in the following paragraphs. Based on Eq. (3), the dual-continuum behavior of the test sample can be characterized by determining parameter B. To implement this technology, the log of $F(t)\Delta P_D$ is first plotted against time, and it is determined whether the curve has a linear relationship with time. If it is the case, the rock sample is a dual continuum system. For a dual-continuum rock sample, the slop of the linear curve ($\ln(F(t)\Delta p_D)$ versus t) is used to estimate the apparent mass transfer coefficient B through Eq. (3). It should be noted that the pore volume needs to be estimated independently. The permeability of the test sample also needs to be estimated through the linear curve fit into the early pressure data; when the dual-continuum behavior can be practically ignored. The following equation is used to estimate the permeability:

$$\ln(\Delta p_D) = -st + C_4 \quad (8)$$

where $C_4$ is a constant and $$s = -\frac{kA_r}{\mu L V_d c_g} f_1 \quad (9)$$

and parameter $f_1$ is defined as $$f_1 = \frac{(\eta + 1) - 3}{1 + \frac{b}{6}(\eta + 1)} \quad (10)$$

Note that Eq. (8) is derived from Eqs. (34) and (37) when the dual-continuum flow term is small. The dual-continuum behavior can be characterized by the mass balance equation of gas flow within the two continua. In the present model, the mass balance equation of gas flow is described as:

$$\frac{\partial q}{\partial x} = -A\frac{\partial p}{\partial t} + q_{im} \quad (11)$$

where t is time, x is the spatial coordinate along the longitudinal direction of the test sample, p is the pressure, $q_{im}$ is mass transfer rate (per unit volume of the porous medium) from the immobile continuum to the mobile continuum, and the parameter A is written as:

$$A = \phi\frac{d\rho}{dp} + (1 - \phi)\frac{d\rho_a}{dp} \quad (12)$$

where ϕ is porosity, $\rho_a$ and $\rho$ are absorption gas density and free gas density, respectively. For a pulse-decay permeability measurement, only the density change is considered while neglecting the porosity change, since a small pulse is imposed in the PDP measurements that test sample can be treated as a rigid medium. Parameter A can also be treated as a constant in the later time of pulse-decay permeability measurement since the gas pressure is almost uniform distributed across the whole system.

The gas mass flux within the test sample for the PDP measurement is described by Darcy's law:

$$q = -\frac{k\rho}{\mu}\frac{\partial p}{\partial x} = -K\frac{\partial p}{\partial x} \quad (13)$$

where k and μ are gas permeability and viscosity, respectively, and K is gas flow conductivity. During the pulse-decay permeability measurement, pressure along the test sample can be treated to be a linear function of the position which is proved by Liu et al. (2016):

$$p = p_u + \frac{p_d - p_u}{L}x = p_u + \frac{\Delta p}{L}x \quad (14)$$

Inserting Eq. (14) into Eq. (13) and then integrating Eq. (13) gives:

$$q = q_0 - A\left[\frac{dp_u}{dt}x + \frac{1}{2}\frac{x^2}{L}\frac{d(\Delta p)}{dt}\right] + q_{im}x \quad (15)$$

where $q_0$ is the gas mass flux at the inlet of test sample (x=0). The gas flux at the outlet, $q_L$, can be obtained from Eq. (15) using x=L:

$$q_L = q_0 - AL\left[\frac{dp_u}{dt} + \frac{1}{2}\frac{d(\Delta p)}{dt}\right] + q_{im}L \quad (16)$$

Combining Eqs. (15) and (13) yields:

$$-K\frac{\partial p}{\partial x} = q_0 - A\left[\frac{dp_u}{dt}x + \frac{1}{2}\frac{x^2}{L}\frac{d(\Delta p)}{dt}\right] + q_{im}x \quad (17)$$

Integrating the previous equation from x=0 to x=L and considering $p=p_u$ at x=0 and $p=p_d$ at x=L, one can obtain:

$$q_0 = \frac{K}{L}(p_u - p_d) + AL\left[\frac{1}{2}\frac{dp_u}{dt} + \frac{1}{6}\frac{d(\Delta p)}{dt}\right] - \frac{1}{2}Lq_{im} \quad (18)$$

Combining Eqs. (16) and (18) gives:

$$q_L = \frac{K}{L}(p_u - p_d) - AL\left[\frac{1}{2}\frac{dp_u}{dt} + \frac{1}{6}\frac{d(\Delta p)}{dt}\right] - \frac{AL}{6}\frac{d(\Delta p)}{dt} + \frac{1}{2}Lq_{im} \quad (19)$$

Then from Eqs. (18) and (19), $$q_0 + q_L = \frac{2K}{L}(p_u - p_d) + \frac{AL}{6}\frac{d(p_u - p_d)}{dt} \quad (20)$$

The gas compressibility $c_g$ is expressed as:

$$c_g = -\frac{1}{\rho}\frac{d\rho}{dp} \tag{21}$$

and the gas mass flux at the inlet and outlet of the sample are expressed as:

$$q_0 = -\frac{V_u c_g \rho_u}{A_r}\frac{dp_u}{dt} \tag{22}$$

$$q_L = \frac{V_d c_g \rho_d}{A_r}\frac{dp_d}{dt} \tag{23}$$

Assuming $$\Delta p = p_u - p_d \text{ and } \Delta V = V_u - V_d \tag{24}$$

Then, taking Eqs. (22), (23) and (24) into (20), Eq. (20) can be rewritten as:

$$-\frac{V_u c_g \rho_u}{A_r}\frac{dp_u}{dt} + \frac{V_d c_g \rho_d}{A_r}\frac{dp_d}{dt} = \frac{2K}{L}\Delta p + \frac{AL}{6}\frac{d\Delta p}{dt} \tag{25}$$

For a small pressure variation during the PDP measurement, the gas density of the upstream reservoir can be assumed to be equal to the downstream reservoirs ($\rho_u = \rho_d$), and Eq. (25) can be rewritten as:

$$\frac{\Delta V c_g \rho_u}{A_r}\frac{dp_u}{dt} = -\left(\frac{AL}{6} + \frac{V_d c_g \rho_u}{A_r}\right)\frac{d\Delta p}{dt} - \frac{2K}{L}\Delta p \tag{26}$$

Combining Eqs. (19), (22), (23) and (24), gives:

$$-\left(\frac{V_u c_g \rho_u}{A_r} + \frac{AL}{2}\right)\frac{dp_u}{dt} = -\frac{AL}{6}\frac{d(\Delta p)}{dt} + \frac{K}{L}\Delta p - \frac{1}{2}Lq_{im} \tag{27}$$

Assuming $$\gamma = \frac{c_g \rho_u}{A_r} \tag{28}$$

and $$\eta = \frac{\frac{\Delta V c_g \rho_u}{A_r}}{\frac{V_u c_g \rho_u}{A_r} + \frac{AL}{2}} = \frac{\Delta V \gamma}{V_u \gamma + \frac{AL}{2}} \tag{29}$$

Eq. (26) can be transformed to:

$$\Delta V\gamma\frac{dp_u}{dt} = -\left(\frac{AL}{6} + V_d\gamma\right)\frac{d\Delta p}{dt} - \frac{2K}{L}\Delta p \tag{30}$$

and Eq. (27) can be rewritten as:

$$-\Delta V\gamma\frac{dp_u}{dt} = \eta\left(-\frac{AL}{6}\frac{d(\Delta p)}{dt} + \frac{K}{L}\Delta p - \frac{L}{2}q_{im}\right) \tag{31}$$

Combining Eq. (30) and Eq. (31), yields:

$$\left(V_d\gamma + \frac{AL}{6}(\eta + 1)\right)\frac{d\Delta p}{dt} = \frac{(\eta - 2)K}{L}\Delta p - \frac{\eta L}{2}q_{im} \tag{32}$$

Denoting $$T = V_d\gamma + \frac{AL}{6}(\eta + 1) \tag{33}$$

Eq. (32) can be transformed to:

$$\frac{d(\ln\Delta p)}{dt} - \frac{(\eta - 2)K}{LT} = -\frac{\eta L}{2T}\frac{q_{im}}{\Delta p} \tag{34}$$

The second term in the left side of Eq. (34) is expressed as:

$$\frac{(\eta - 2)K}{LT} = \frac{k\rho}{\mu L}\frac{(\eta + 1) - 3}{V_d\gamma + \frac{AL}{6}(\eta + 1)} \tag{35}$$

Denoting $$c = \frac{AL}{V_d\gamma} = \frac{\phi + (1 - \phi)k_a}{V_d}LA_r \tag{36}$$

Eq. (35) can be rewritten as:

$$\frac{(\eta - 2)K}{LT} = \frac{kA_r}{\mu L V_d c_g}\frac{(\eta + 1) - 3}{1 + \frac{c}{6}(\eta + 1)} \tag{37}$$

If there is no absorption gas for the test sample, parameter c in Eqs. (36) and (37) is equal to b in Eq. (7). Further, Eq. (34) can be simplified as:

$$F(t)\Delta p = -\frac{\eta L}{2T}q_{im} \tag{38}$$

where $$F(t) = \frac{d(\ln\Delta p)}{dt} - \frac{(\eta - 2)K}{LT} \tag{39}$$

For a dual-continuum rock matrix, the mass transfer between the two continua is assumed to be uniformly distributed for the PDP measurement and only treated as a function of time. Therefore, the mass transfer rate can be expressed as:

$$q_{im} = -\frac{\partial \rho_{m,i}}{\partial t} = -C^* e^{-Bt} \quad (40)$$

where C* is a constant (which is just B*C from Eq. (7)). During the PDP measurement, the gas flows from the upstream reservoir to downstream reservoir by passing through the test sample. The gas first propagates into the mobile continuum of the test sample so that the pressure in the mobile continuum is greater than the pressure in the immobile continuum and gas transfers from the mobile continuum to the immobile continuum (that is, $q_{im}$<0). Therefore, $q_{im}$<0 means gas flows from the mobile continuum to the immobile continuum, which causes pressure difference (between the upstream and downstream reservoirs) curve to bend upwards in the late time of pulse-decay measurement. Conversely, it would bend downwards for $q_{im}$>0 (gas transfers from the immobile continuum into the mobile continuum).

Taking Eq. (40) into Eq, (38), the Eq. (38) can be rewritten as $$F(t)\Delta p = -\frac{\eta L}{2T} q_{im} = \frac{\eta L}{2T} C^* e^{-Bt} \quad (41)$$

Taking the log of both sides of Eq. (41), it gives $$\ln(F(t)\Delta p) = -Bt + C_2 \quad (42)$$

where $$C_2 = \ln\left(\frac{\mu L C^*}{2T}\right) \quad (43)$$

Denoting $$\Delta p_D = \frac{\Delta p}{\Delta p_{pulse}} \quad (44)$$

Eq. (42) can be rewritten as:

$$\ln(F(t)\Delta p_D) = -Bt + C_3 \quad (45)$$

where $$C_3 = C_2 - \ln(\Delta p_{pulse}) \quad (46)$$

Therefore, Eq. (45) shows that there is a linear relation between $\ln(F(t)\Delta p)$ and the measurement time t for the a dual-continuum test sample. Eq. (45) can further be used to estimate the apparent mass transfer coefficient B by analyzing the test data.

The following table shows an example list of parameters used for testing a shale sample and the experimental conditions for performing the PDP measurement, according to one or more example embodiments.

| Parameter | Value |
|---|---|
| Initial upstream pressure (psi) | 2618 |
| Initial downstream pressure (psi) | 2509 |
| Upstream reservoir volume (cubic centimeter, cc) | 11.9992 |
| Downstream reservoir volume (cc) | 0.8483 |
| Diameter of the rock sample (centimeter, cm) | 2.527 |

-continued

| Parameter | Value |
|---|---|
| Length of the rock sample (cm) | 5.1 |
| Pore volume of the test sample (cc) | 0.4203 |
| Confining pressure of the rock sample (psi) | 3000 |
| Temperature (° C.) | 49.41 |
| Flow gas type | Nitrogen |

Figure 6A:
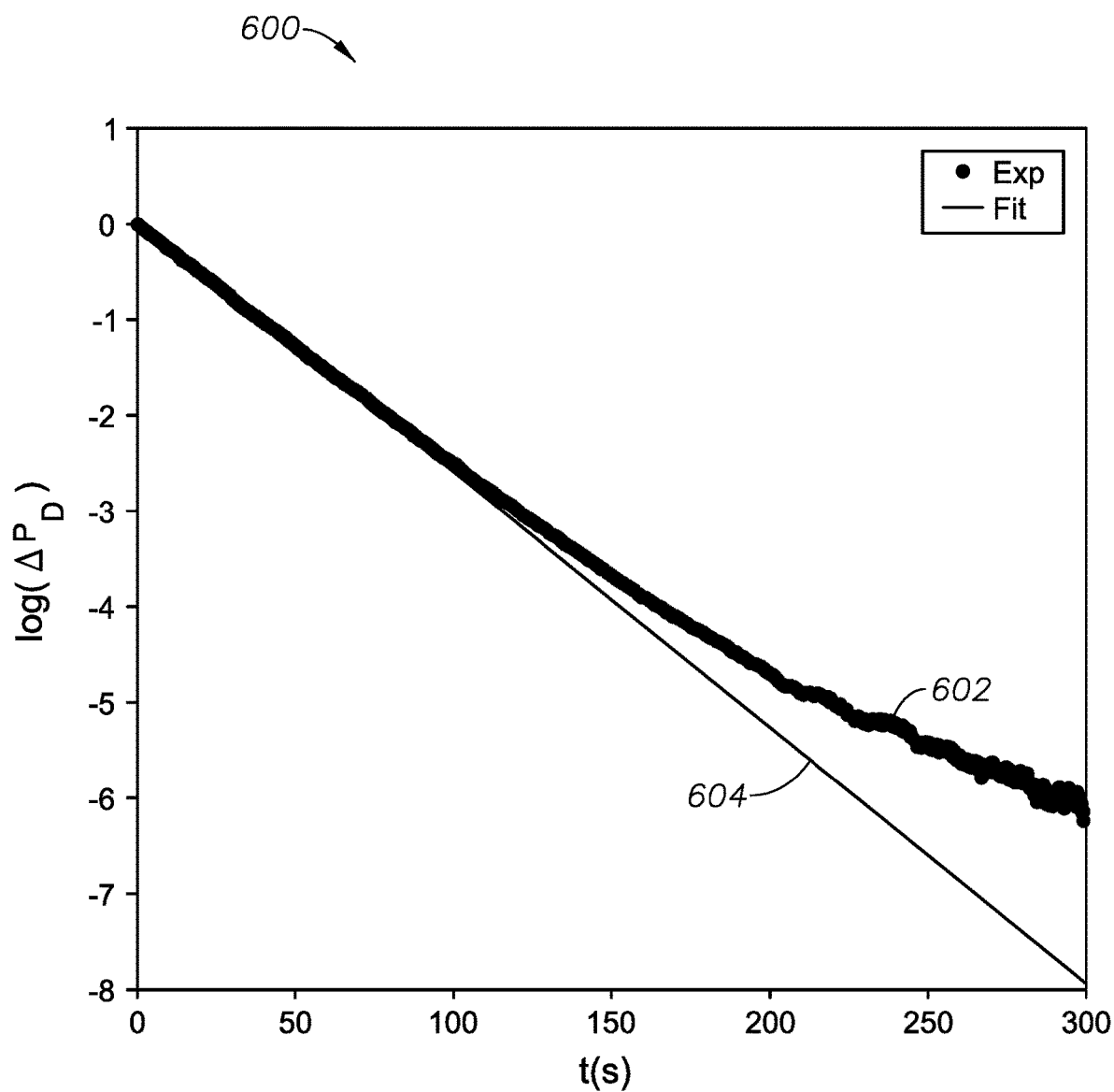
FIG. 6A is a linear curve plotting $\log(\Delta P_D)$ versus time to estimate the permeability of a test core sample, according to one or more example embodiments.
Figure 6B:
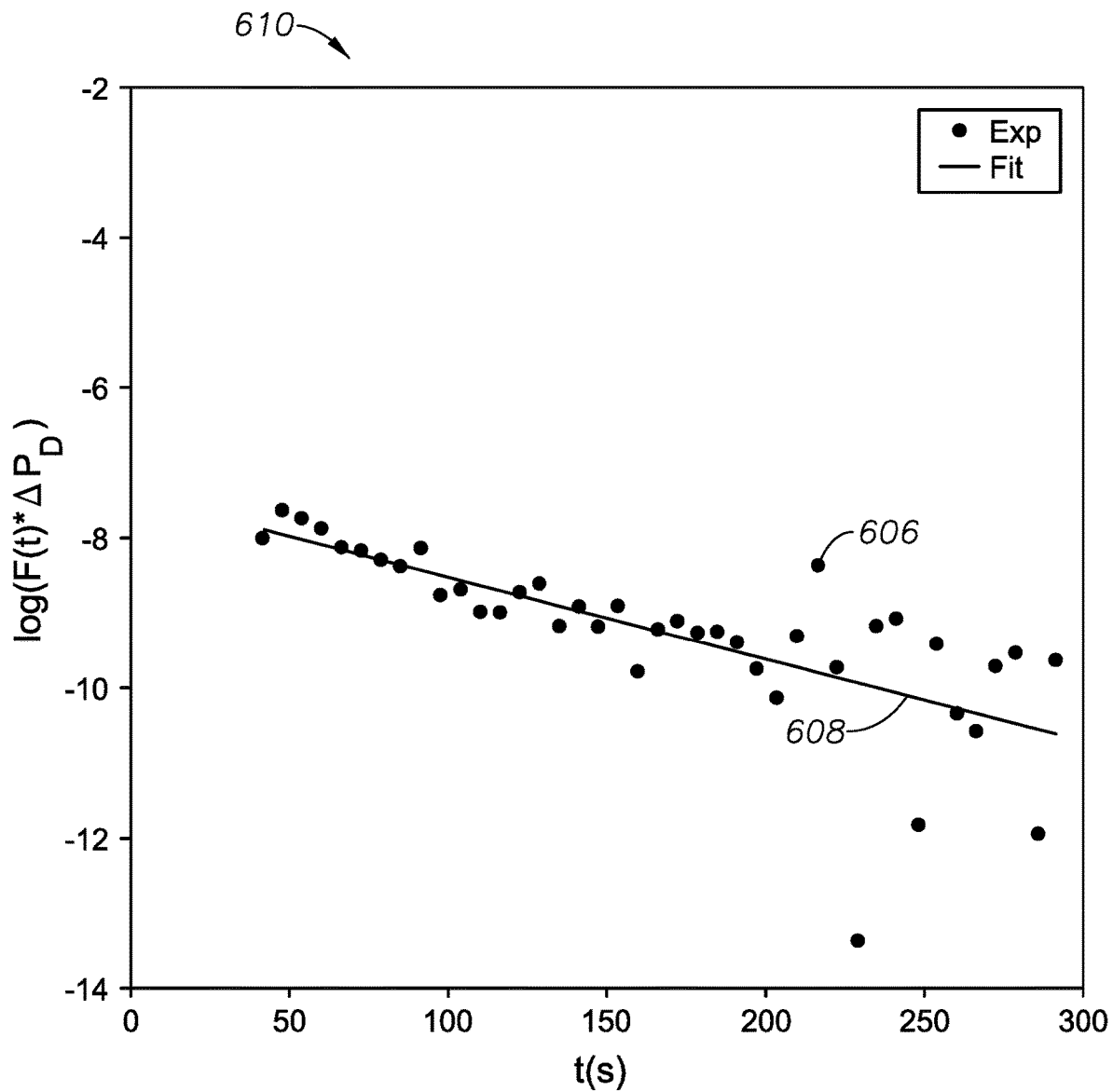
FIG. 6B is a linear curve plotting $\log(F(t)\Delta P_D)$ versus time to estimate the apparent mass transfer coefficient 'B' for the dual-continuum system, according to one or more example embodiments.

FIG. 6A is a linear curve 600 plotting $\log(\Delta P_D)$ versus time to estimate the permeability of a test core sample, according to one or more example embodiments. FIG. 6B is a linear curve 610 plotting $\log(F(t)\Delta P_D)$ versus time to estimate the apparent mass transfer coefficient 'B' for the dual-continuum system, according to one or more example embodiments. In this section it is shown how to practically implement the proposed workflow with an application example. FIG. 6A illustrates $\log(\Delta p_D)$ versus time and FIG. 6B illustrates $\log(F(t)\Delta p_D)$ versus time for the test sample. The permeability value of the sample is estimated as 3195 nanoDacrys (nD) by using Eq. (8). Then, the porosity and permeability values are taken as input parameters for plotting points 606 of $\log(F(t)\Delta p_D)$ versus t (see FIG. 6B). It can be observed here that the curve 602 in FIG. 6A is bending up in the late time of the PDP measurement, as well as a linear relation 608 for points 606 in FIG. 6B. They indicate that the test sample is a dual-continuum system. Finally, the apparent mass transfer coefficient B is calculated as 0.013 ($s^{-1}$) by using Eq. (24) (see FIG. 6B). The straight line 604 in FIG. 6A shows the linear curve fitting to estimate the permeability of the test core sample, and the straight line 608 in FIG. 6B represents linear curve fit for $\log(F(t)\Delta P_D)$ versus time. The slop of the straight line 608 in FIG. 6B can be used to estimate the apparent mass transfer coefficient B for the dual-continuum system, according to one or more example embodiments of the present disclosure.

The present disclosure provides an advanced methodology to measure the apparent mass transfer coefficient of the dual-continuum system. Prior approaches are limited to the same volumes for the upstream and downstream reservoirs in the PDP setups. In summary, non-limiting advantages of this new technique include: (1) it utilizes the widely-used PDP measurements, and thus can be applied as a routine to check the dual-continuum behavior of a test sample when measuring its permeability; (2) it allows to estimate the apparent mass transfer coefficient B from the pulse-decay measurements with different volumes of the upstream and downstream reservoirs; (3) the procedure to examine the dual-continuum behavior is straightforward since it only needs to check the linearity of the related curve; (4) the apparent mass transfer coefficient for a dual-continuum system can be easily estimated from the slope of the linear curve.

The Specification, which includes the Summary, Brief Description of the Drawings and the Detailed Description, and the appended Claims refer to particular features (including process or method steps) of the disclosure. Those of skill in the art understand that the disclosure includes all possible combinations and uses of particular features described in the Specification. Those of skill in the art understand that the disclosure is not limited to or by the description of embodiments given in the Specification.

Those of skill in the art also understand that the terminology used for describing particular embodiments does not limit the scope or breadth of the disclosure. In interpreting the Specification and appended Claims, all terms should be interpreted in the broadest possible manner consistent with the context of each term. All technical and scientific terms used in the Specification and appended Claims have the same meaning as commonly understood by one of ordinary skill in the art to which this disclosure belongs unless defined otherwise.

As used in the Specification and appended Claims, the singular forms "a," "an," and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced.

Conditional language, such as, among others, "can," "could," "might," or "may," unless specifically stated otherwise, or otherwise understood within the context as used, is generally intended to convey that certain implementations could include, while other implementations do not include, certain features, elements, or operations. Thus, such conditional language generally is not intended to imply that features, elements, or operations are in any way required for one or more implementations or that one or more implementations necessarily include logic for deciding, with or without user input or prompting, whether these features, elements, or operations are included or are to be performed in any particular implementation.

The systems and methods described in this disclosure, therefore, are well adapted to carry out the objects and attain the ends and advantages mentioned, as well as others that may be inherent. While example embodiments of the system and method have been given for purposes of disclosure, numerous changes exist in the details of procedures for accomplishing the desired results. These and other similar modifications may readily suggest themselves to those skilled in the art, and are intended to be encompassed within the spirit of the system and method disclosed here and the scope of the appended claims.

The invention claimed is:

1. A method of determining a flow characteristic of a subterranean reservoir formation for the purpose of predicting production capabilities, the method comprising the steps of:
    obtaining a reservoir sample from the subterranean reservoir formation;
    placing the reservoir sample in a sample holder, where the reservoir sample is fluidly connected to an upstream gas reservoir and a downstream gas reservoir;
    filling the upstream gas reservoir, the downstream gas reservoir, and the reservoir sample with a gas to a gas pressure such that the gas pressure in the upstream gas reservoir, the downstream gas reservoir and the sample is uniform;
    closing an upstream valve, where closing the upstream valve isolates the upstream gas reservoir from both the downstream gas reservoir and the sample;
    closing a downstream valve, where closing the downstream valve isolates the downstream gas reservoir from both the upstream gas reservoir and the sample;
    increasing the pressure in the upstream gas reservoir to a test pressure;
    opening the upstream valve at the same time creating a pressure pulse that is transported from the upstream reservoir to the downstream reservoir by passing through the sample;
    measuring the pressure data in the upstream gas reservoir and the downstream gas reservoir;
    obtaining from the reservoir sample dual-continuum test data, wherein the dual-continuum data comprises first stage pressure data that is different from second stage pressure data;
    determining a mass transfer coefficient from the dual-continuum test data; and
    determining the flow characteristic from the mass transfer coefficient.

2. The method of claim 1, the dual-continuum test data comprises second stage or late-time stage pressure data.

3. The method of claim 1, where the subterranean formation is selected from the group consisting of limestone, sandstone, and shale.

4. The method of claim 1, where the dual-continuum test data is obtained from a dual-continuum test system.

5. The method of claim 1, wherein a volume of the upstream reservoir is different from a volume of the downstream reservoir.

6. The method of claim 1, wherein the flow characteristic is dual-continuum flow.

7. The method of claim 1, wherein the flow characteristic is a function of an immobile continuum and a mobile continuum in the reservoir sample.

8. The method of claim 1, further comprising:
    generating single-continuum test data if dual-continuum behavior is absent.

* * * * *